United States Patent
Bernard (10) Patent No.: US 10,092,262 B2
(45) Date of Patent: Oct. 9, 2018

(54) METHOD AND SYSTEM FOR TOMOSYNTHESIS PROJECTION IMAGES ENHANCEMENT

(71) Applicant: GENERAL ELECTRIC COMPANY, Schenectady, NY (US)

(72) Inventor: Sylvain Bernard, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 218 days.

(21) Appl. No.: 14/984,846

(22) Filed: Dec. 30, 2015

(65) Prior Publication Data

US 2016/0183901 A1 Jun. 30, 2016

(30) Foreign Application Priority Data

Dec. 31, 2014 (GB) .................................. 1423370.4

(51) Int. Cl.
*A61B 6/00* (2006.01)
*A61B 6/02* (2006.01)
*G06T 11/00* (2006.01)

(52) U.S. Cl.
CPC ............ *A61B 6/5205* (2013.01); *A61B 6/025* (2013.01); *A61B 6/502* (2013.01); *A61B 6/5258* (2013.01); *A61B 6/542* (2013.01); *G06T 11/005* (2013.01); *G06T 2211/436* (2013.01)

(58) Field of Classification Search
CPC ....... A61B 6/5205; A61B 6/025; A61B 6/502; A61B 6/5258; A61B 6/542; G06T 11/005; G06T 2211/436
See application file for complete search history.

(56) References Cited

U.S. PATENT DOCUMENTS

| 4,903,204 A * | 2/1990 | Dobbins, III | G06T 11/006 378/4 |
| 7,978,895 B2 * | 7/2011 | Wang | G06T 11/008 382/128 |
| 8,774,355 B2 * | 7/2014 | Claus | G06T 11/005 378/21 |
| 2002/0131549 A1 * | 9/2002 | Oikawa | G06T 11/005 378/19 |
| 2007/0116343 A1 | 5/2007 | Sauer et al. | |
| 2007/0183564 A1 * | 8/2007 | Li | A61B 6/025 378/22 |

(Continued)

FOREIGN PATENT DOCUMENTS

| GB | 2453177 A1 | 4/2009 |
| WO | 2015054518 A1 | 4/2015 |

OTHER PUBLICATIONS

Combined Search and Exam Report for corresponding GB Appln. No. 1423370.4, dated Jul. 1, 2015, 5 pages.

*Primary Examiner* — Kim Vu
*Assistant Examiner* — Molly Delaney (57) ABSTRACT

Method and system for obtaining images of an object of interest using a system comprising an x-ray source facing a detector. The method and system enable the acquiring of a plurality of 2D projection images of the object of interest in a plurality of orientations. A selected 2D projection image such as the zero projection of the plurality of projections can be enhanced by using at least a subset of the plurality of tomosynthesis projection images. The obtained enhanced 2D projection image is displayed for review.

18 Claims, 5 Drawing Sheets

(56) References Cited

U.S. PATENT DOCUMENTS

| | | | |
|---|---|---|---|
| 2007/0242868 A1* | 10/2007 | Stanton | G01N 23/046 382/131 |
| 2008/0100612 A1* | 5/2008 | Dastmalchi | A61B 3/102 345/418 |
| 2009/0123048 A1* | 5/2009 | Leroux | G06T 11/006 382/131 |
| 2009/0123052 A1 | 5/2009 | Ruth et al. | |
| 2010/0135558 A1* | 6/2010 | Ruth | G06T 11/006 382/131 |
| 2011/0150178 A1* | 6/2011 | Bernard | G06T 11/008 378/22 |
| 2015/0201890 A1* | 7/2015 | Maidment | A61B 6/025 382/131 |

* cited by examiner

METHOD AND SYSTEM FOR TOMOSYNTHESIS PROJECTION IMAGES ENHANCEMENT

BACKGROUND

The present disclosure relates to the field of tomosynthesis and to a method and system for processing tomosynthesis imaging data for obtaining enhanced projection images.

X-ray imaging systems have become a valuable tool in medical applications such as for the diagnosis of many diseases. As standard screening for breast cancer mammography 2-dimensional (2D) x-ray images are taken across the entire breast tissue. These known 2D mammograms are limited by tissue superimposition. That is to say, lesions may be masked by the tissue above or underneath, or normal structures may mimic a lesion. In order to minimize limitations of standard 2D-mammography caused by tissue superimposition, digital breast tomosynthesis using digital receptors has been developed.

The tomosynthesis systems employ at least one x-ray tube, which is moved in an arc above a stationary detector. In digital breast tomosynthesis (DBT) the volume information of an object of interest can be derived from a series of images, known as projection images or projections, which are taken at various angles by means of one or more x-ray sources. Objects of different heights in a breast display differently in the different projections. From the 2D projection images 3D volumes can be generated for review. The generated 3D volume portions offer advantages to overcome the limitations associated with tissue superimposition.

During the adaption period of the tomosynthesis technology, the provision of the known 2D mammography is still desired by medical professional or radiologist, who want to use existing expertise gained from reviewing 2D mammograms. Furthermore, archived 2D-mammograms can be better compared with images obtained with the same technology than with images of a new modality as tomosynthesis. To address the need for 2D mammograms besides the provision of the relatively recent tomosynthesis images, it is known to perform a combo acquisition of images. That is to say both the known 2D mammography and digital breast tomosynthesis are acquired for the same object of interest. However, since the average dose from tomosynthesis imaging is approximately the same as the known mammogram 2D imaging, the radiation exposure is roughly doubled. Thus, there is the need, to generate or acquire the information of known 2D mammograms without performing two examinations, in order to reduce the dose.

One problem to be addressed is that images acquired during tomosynthesis through digital receptors may be contaminated by a variety of noise sources. By noise we refer to stochastic variations as opposed to deterministic distortions such as lack of focus. One drawback is that a single tomosynthesis projection image at a given orientation or x-ray source position is very noisy because the dose per projection is not enough to be compared to a known 2D mammogram acquisition. Accordingly, there is a need to improve image quality comprising noise management in order to offer a tomosynthesis 2D image that looks like a known full-dose 2D mammogram in order to enable high quality diagnostic.

Further, there is the need to facilitate lesion identification by a health professional by providing further reviewing modalities, wherein not only one 2D image but also one or more 3D images are provided. This addresses the need for possible navigation and smooth transition from 2D to 3D images.

SUMMARY OF THE INVENTION

In one aspect, the present disclosure is directed to a method for obtaining at least one enhanced image of an object of interest using a system comprising an x-ray source facing a detector. The method comprises acquiring a plurality of 2D tomosynthesis projection images of the object of interest in a plurality of orientations; enhancing a selected projection image of the plurality of projections using at least a subset of the plurality of tomosynthesis projection images; and displaying the enhanced 2D projection image.

The enhanced 2D images provide an overview of the object of interest such that a health professional can review a patient's breast in one viewing.

According to an embodiment of the disclosure the enhancing step further comprises, for each pixel (i,j) of the selected projection image and for a given height accumulating the values of the corresponding pixel position in at least one of the tomosynthesis projections, ranking the accumulated values for each pixel over all possible heights; determining the most likely height for each pixel (i,j) by selecting the maximum accumulated value; and combining (i,j)'s level with the determined maximum values for each pixel (i,j).

Said determined maximum values are corresponding to maximum accumulated values. The level of pixel (i,j) or (i,j)'s level corresponds to (i,j)'s gray level intensity in the image. The accumulation process for each pixel (i,j) of the selected projection image can be a summation, averaging or any non-linear combination. The accumulation process can be a summation, averaging or any non-linear combination. In a particular embodiment, one can average the values among all the projections excluding the most contrasting value. By excluding the most contrasting value, artefacts introduced by highly contrasted objects are reduced.

In another aspect, the method step of accumulating is performed for different frequency bands obtained by filtering the projection images. In this way the different sizes of objects such as calcifications, fibers, masses and glands may be taken into account. By filtering, undesired artifacts can be avoided.

According to another embodiment the most likely height of each pixel (i,j) is stored as a height map associated to the enhanced 2D projection image.

According to yet another embodiment of the disclosure the most likely height of each pixel (i,j) is obtained as a combination of maximum accumulated value and 3D marks provided by a CAD system or indicated by a user through a 3D review system. In another embodiment, the method receives 3D findings locations as input. When pixel (i,j) is part of at least one finding's projection (the projection being performed on the image to be enhanced), the height associated to (i,j) becomes the finding's height. The height map is then modified accordingly. The value to be combined with the original (i,j)'s level becomes the accumulated value for the finding's height.

According to another embodiment of the disclosure the selected projection image is the central projection (0°), which is the projection perpendicular to or closest to the perpendicular of the detector. The central projection has advantageously the same geometry as a known 2D mammogram. In case the object of interest is a patient's breast a 2D breast overview comparable to a known 2D mammogram is provided.

In yet another aspect of the disclosure at least one tomosynthesis projection image is denoised prior to improving the image quality of at least one of said at least one tomosynthesis projection image. By way of example, directional filtering can be applied as one denoising method.

In another aspect, the method according to the disclosure further comprises enhancing the tomosynthesis projection images for each of the plurality of orientations; projecting each enhanced image on an isocentric virtual detector, wherein the normal to the virtual detector points towards the source position; and displaying successively the virtual projections.

Advantageously, the successive display provides an improved rendering effect wherein the user can quickly appreciate the breast content looking at different angulations. Preferably, the successive display is performed with an adjustable speed.

In another aspect, the present disclosure is directed to a computer program product, wherein the computer program product comprises program instructions for carrying out each of the method steps of the disclosure, when said product is executed on a computer.

In yet another aspect, the present disclosure is directed to a computer readable medium storing program instructions, which, when executed by a processor of a computer cause the computer to perform each of the method steps of the disclosure. In general a computer-readable medium may be, for example, a hard disk, a CD-ROM, diskette, a ROM/RAM memory, DVD, a digital source such as a network or the internet or any other suitable means.

In yet another aspect, the disclosure is directed to a system for obtaining enhanced images of an object of interest. The system comprises an imaging system comprising an x-ray source and a detector configured to acquire a plurality of 2D tomosynthesis projection images of the object of interest such as a patient's breast; a processing unit configured to compute for a selected projection image of the plurality of projection images an enhancement using at least a subset of the plurality of projections; and a display unit configured to display the enhanced projection image.

At least one of the above embodiments provides one or more solutions to the problems and disadvantages of the background art. One technical effect that may be realized in the practice of all or some embodiments of the described methods and systems is to reduce radiation dose and improve at the same time dataflow and workflow efficiencies. Other technical advantages of the present disclosure will be readily apparent to one skilled in the art from the following description and claims. Various embodiments of the present application obtain only a subset of the advantages set forth. No single advantage is critical to the embodiments. Any claimed embodiment may be technically combined with any other claimed embodiments.

BRIEF DESCRIPTION OF THE DRAWINGS

The accompanying drawings illustrate exemplary embodiments of the disclosure and serve to explain, by way of example, the principles of the disclosure.

DETAILED DESCRIPTION

Figure 1:
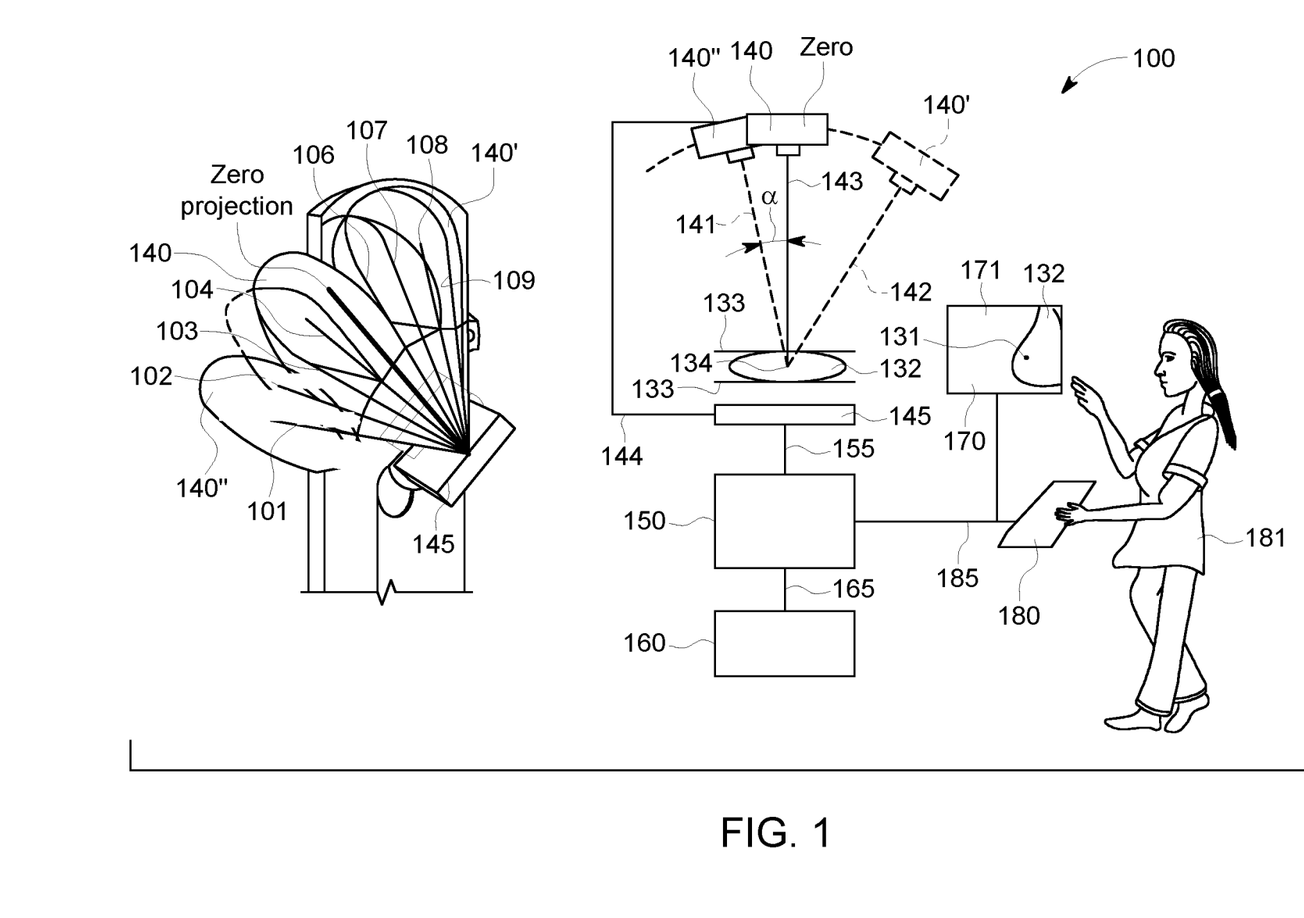
FIG. 1 is a diagrammatic illustration and a perspective partial view of an imaging system according to an exemplary embodiment of the disclosure.

FIG. 1 is a diagrammatic illustration 1 of a system for obtaining an enhanced projection image of an object of interest, wherein the system 100 comprises a x-ray beam source 140 facing the detector 145. The x-ray beam source 140 and the detector 145 are connected by an arm 144. Between the detector 145 and the source 140 an object of interest 132 can be placed. In the system illustrated, the x-ray source 140 moves in an arc above a single detector 145. The detector 145 and a plurality of positions of the x-ray source 140' and 140" following an arc (see dashed line) are shown with dashed/solid lines and in a perspective partial view. In the shown arrangement, the detector 145 is fixed at the shown position and only the x-ray source 140 moves. The angle α is a projection angle enclosed by the zero-orientation and any other orientation such as 141 and 142. In this way multiple different views of the breast tissue can be acquired via the at least one x-ray source 140. The projection of lowest α or the projection closest to the zero-orientation is named the central projection or zero projection by approximation.

Still referring to FIG. 1, on the left side is shown a partial perspective view of an imaging system according to an exemplary embodiment of the disclosure comprising a detector 145 and an x-ray source 140. The different positions of the x-ray source 140, 140' and 140" are broadly depicted to illustrate the movement of the x-ray source. There are nine different projection views 101, 102, 102, 103, 104, 106, 107, 108, 109 including the zero projection (105) indicated as straight lines, which all point to the center of the detector 145.

The patient (not shown) is positioned in front of the mammography arm. To take for example a known mediolateral oblique (MLO) view, the mammography technologist 181 will set the angle for the desired projection (30 degrees to 60 degrees, wherein 45 degree represents the preferred zero projection shown in the perspective view of FIG. 1). During routine screening mammography, the angled MLO view is preferred over a lateral 90-degree projection because more of the breast tissue can be imaged.

The object of interest 132 shown in display unit 170 is a breast compressed by compression paddles 133, which ensure uniform compression and immobilization of the breast during the radiation exposure for optimal image quality. The breast 132 comprises for example a punctual object 131 as a calcification, which is located in the zero orientation 143, which is perpendicular to the detector 145 plane. The user may review calcifications or other clinical relevant structures for diagnosis. The display depicts a known 2D mammography view, where mainly the middle portion of the breast 132 can be reviewed.

The detector 145 and the x-ray source 140 constitute the acquisition unit, which is connected via a data acquisition line 155 to a processing unit 150. The processing unit 150 comprises a memory unit 160, which may be connected via an archive line 165.

A user such as a health professional may input control signals via the user interface 180. Such signals are transferred from the user interface to the processing unit 150 via the signal line 185. The method and system according to the disclosure enables the user to obtain an enhanced 2D projection image that looks like a known 2D mammogram. Based on this high quality image, the radiologist is capable of identifying all the clinical signs relevant for breast screening. Especially if the health professional is used to known 2D mammograms, the user may easily analyze the displayed picture. Further there is the possibility of displaying stored former 2D mammograms for comparison with the one acquired through the new tomosynthesis modality according to the present disclosure. Besides, tomosynthesis images may be reviewed and archived. A CAD system or the user himself can provide 3D marks. A height map of punctual objects or other objects obtained according to an embodiment of the disclosure can be combined with height information provided by 3D marks by a CAD system or indicated by a user through a 3D review system. Further, the user may decide if the 2D full-volume images or other images are archived or not. Alternatively saving and storing of the images may be done automatic ally.

The memory unit 150 can be integral or separate from the processing unit 150. The memory unit 160 allows storage of data such as the 2D enhanced projection image and optionally tomosynthesis 3D images. In general, the memory unit 160 may comprise a computer-readable medium for example a hard disk or a CD-ROM, diskette, a ROM/RAM memory, DVD, a digital source such as a network or the Internet or any other suitable means. The processing unit 150 is configured to execute program instructions stored in the memory unit 160, which cause the computer to perform the methods of the disclosure. One technical effect of performing the method according to the embodiments of the invention is that the x-ray source may be less used, since the enhanced 2D projection image can replace a known 2D mammogram, which usually is based on a separate x-ray exposure in order to get high quality images.

Figure 2:
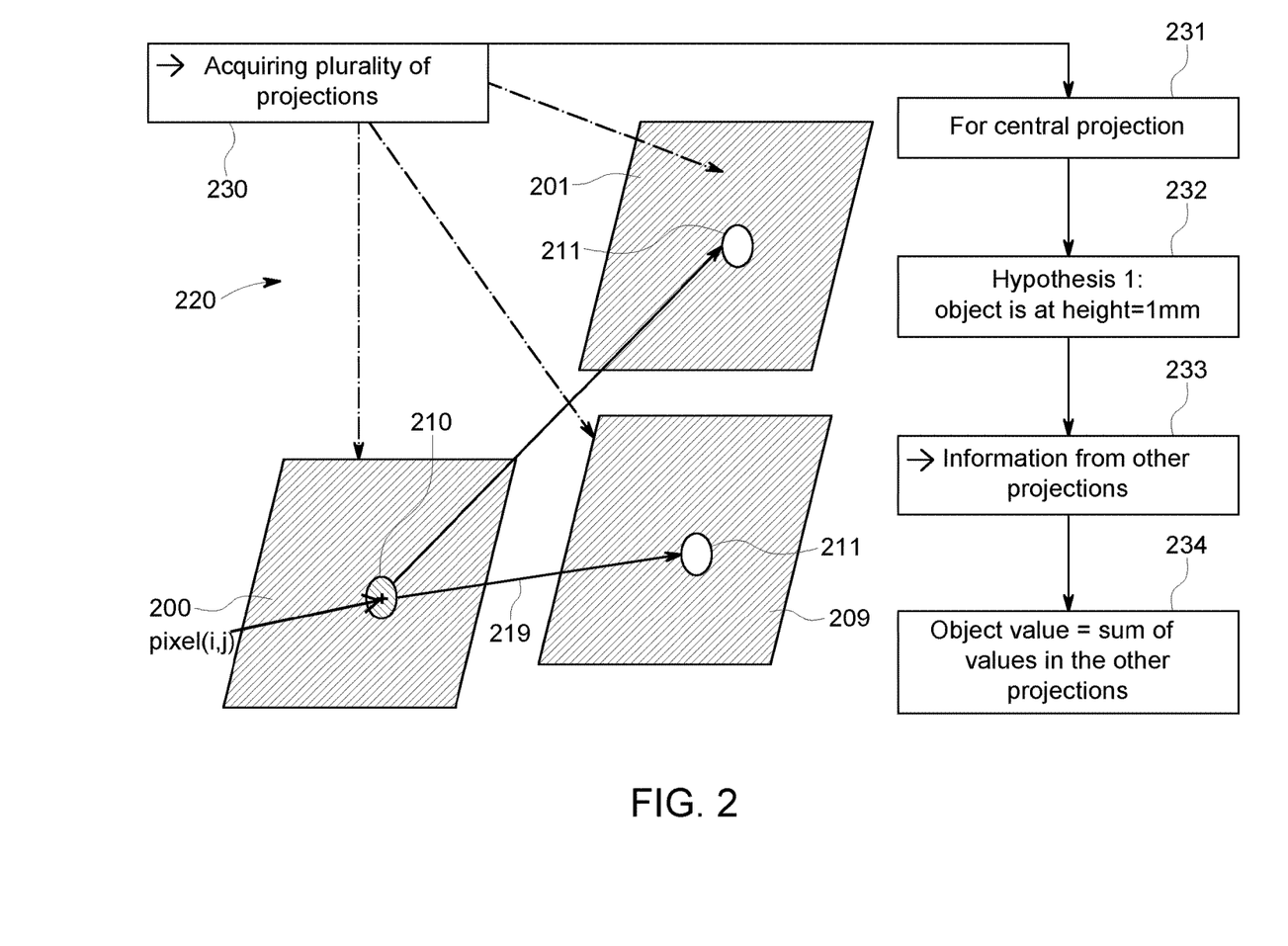
FIG. 2 is a flow chart and diagrammatic illustration of a method according to an exemplary embodiment of the disclosure for obtaining at least one enhanced image of an object of interest.

FIG. 2 illustrates schematically the method 220 according to an embodiment of the disclosure. In a first step, a plurality of 2D projection images are acquired. For example 9 projections can be acquired in step 230. In order to generate an enhanced 2D projection image the central projection is selected in step 231, since this central projection has the same geometry as known 2D mammograms. This central projection advantageously provides the underlying breast content.

However, all projection images are acquired at a low dose, which is many times lower than the dose needed for a known 2D mammogram. This low dose results in low image quality, which needs to be improved or enhanced. In the central projection, a 3D object is a 2D representation of said 3D object 210 including pixel (i,j). Said pixel (i,j) is indicated with the cross in the center of the object 210. Due to the 2D representation of the object 210, the height location of the 3D object within the volume of the breast is not known. The term "height" in this instance shall mean a given altitude or distance of an object in the breast volume relative to or spaced away from the detector. Since the height of the 3D object 210 is not known, the height is guessed or estimated in step 232, wherein as first hypothesis (or starting point) a location of the object is assumed to be at the height of 1 mm. Based on this hypothesis information, at least a subset of the plurality of other projections is retrieved in step 233. This subset or other projections are illustrated schematically by the projections 201 and 209.

In step 234, the object value is calculated by accumulating the values of objects 211 found at 1 mm in the other projections.

Figure 3:
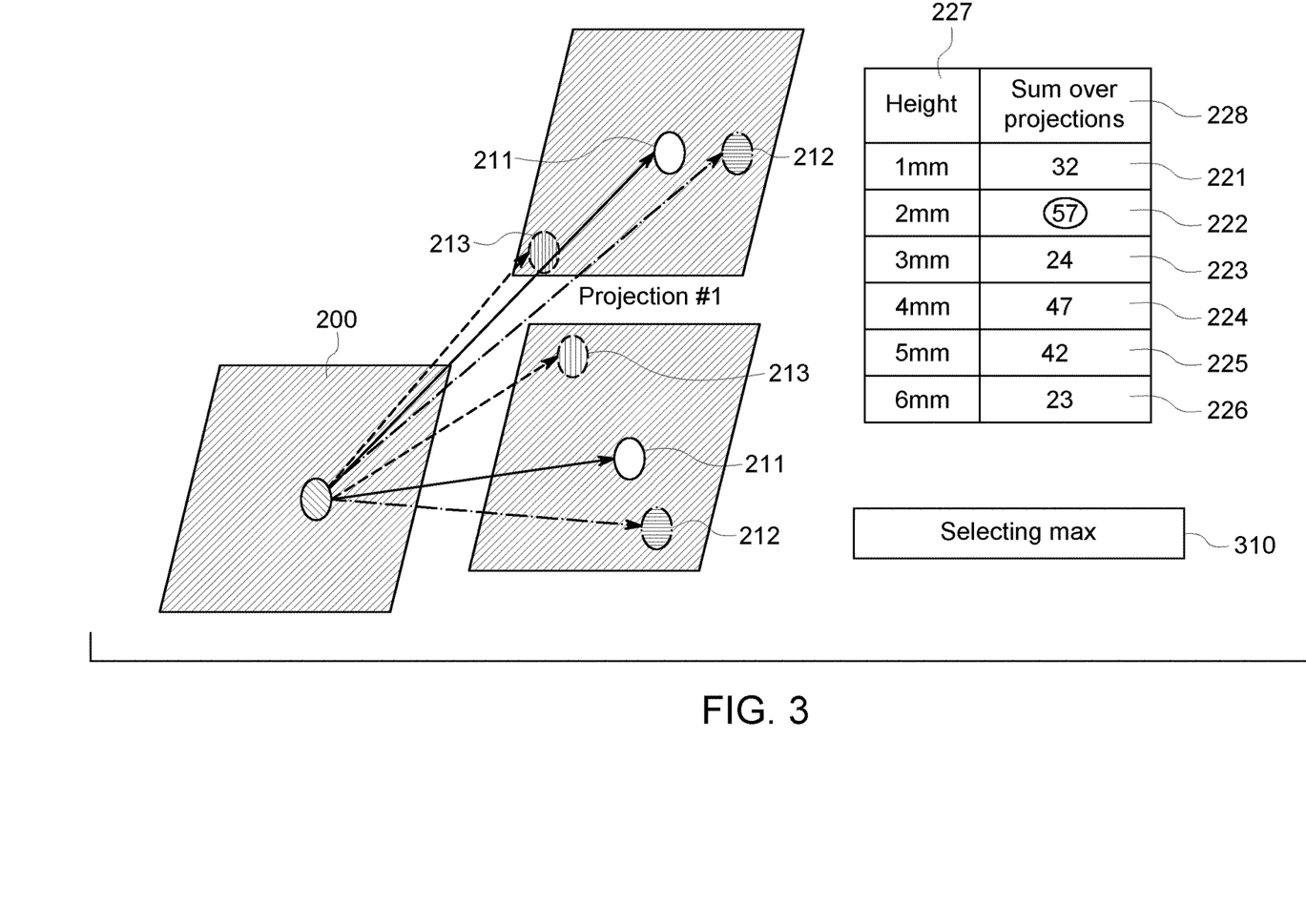
FIG. 3 is a diagrammatic illustration of a method according to another exemplary embodiment of the disclosure.

FIG. 3 shows the last step 234 described in FIG. 2 summarized in a height table. Similar to the first hypothesis, additional hypotheses are made for other heights in 1 mm steps or increments (e.g. 1 mm, 2 mm, 3 mm, etc). The result of each hypothesis at a given height is depicted in the first column 227 comprising different height values and in the second column 228, which lists the sums of values in the other projections (221, 222, 223, 224, 225, 226). This method is schematically shown by the arrows originating from an object or pixel (i,j) and pointing to the corresponding values in other projections (201, 209). The sums are then derived from the values of objects 211, 212, 213 and corresponding pixel positions in the other projections.

In step 310, the maximum value is selected from the accumulated values. That is to say by ranking the accumulated values for each pixel over all possible heights, the most likely height for each pixel (i,j) can be determined. In this context, the term "most likely height" shall mean the estimated or most probable height position or altitude for each pixel (i,j). Since the method to obtain the most likely height is an estimation method, the resulting height is with very high probability the real height of the 3D object within the breast. In the illustrated case, the maximum value of 57 was determined at a height of 2 mm, such that the object is most likely positioned at this height. From this information of the most likely heights of each pixel (i,j), a height map can be generated. This height map can be associated with the enhanced 2D projection image. Said enhanced 2D projection image is obtained by combining the level of pixel (i,j) with the determined maximum values for each pixel (i,j).

Figure 4:
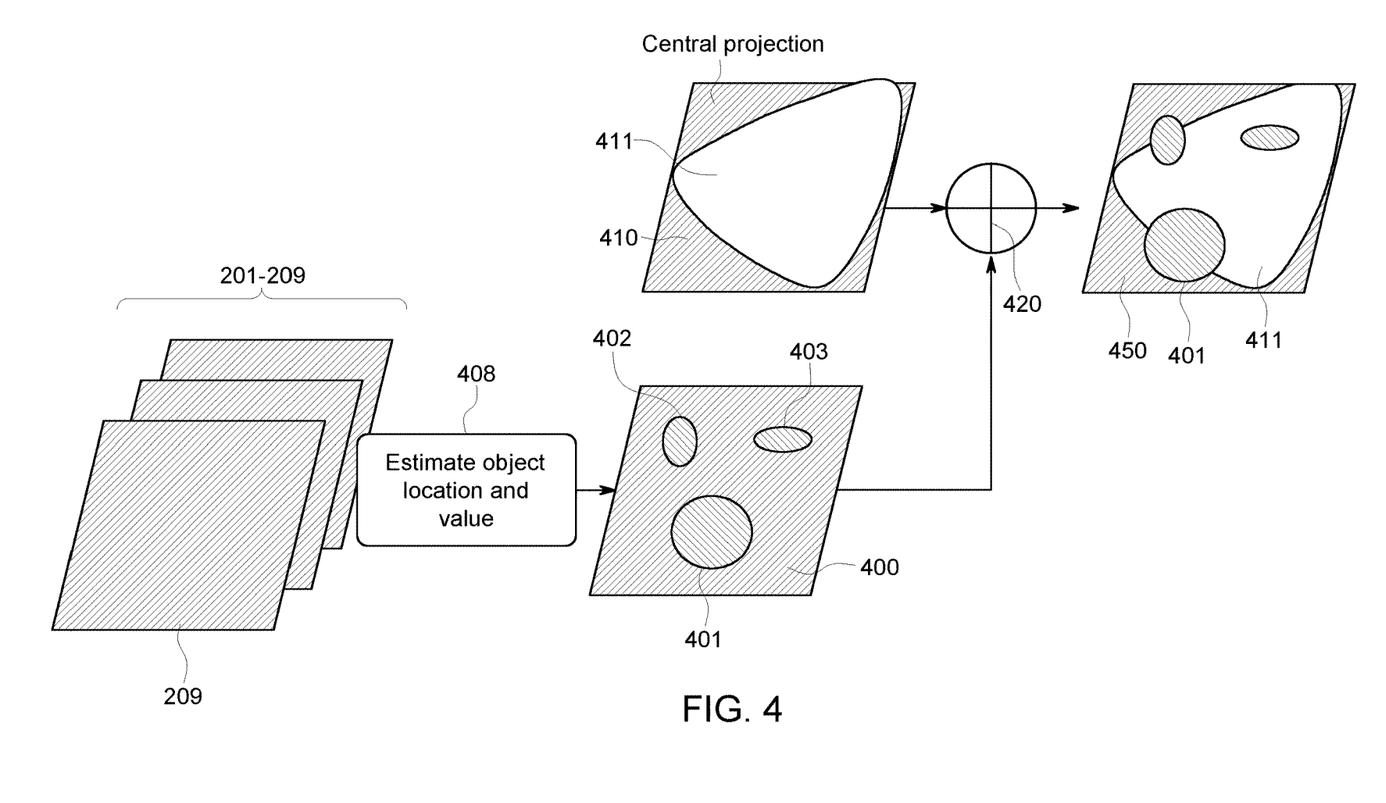
FIG. 4 show flow chart of a method according to another exemplary embodiment of the disclosure.

FIG. 4 shows a flow chart of a method according to another exemplary embodiment of the disclosure. The processing of values of the tomosynthesis projection images (201-209 except the central projection) is performed for different frequency bands corresponding to different object sizes, in order to better image and identify small calcifications or bigger objects as masses. The object location or height of an object of a selected projection and corresponding value is estimated in step 408, based on the information of the other projections (201, . . . 209). Then the determination of the most likely height for each pixel follows by selecting the maximum accumulated value. The projection 400 provides after the height determination step top ranked object values of each pixel. The projection 400 shows objects of different sizes, whereas the central projection 410 schematically shows image data of breast tissue 411.

In step, 420 the central projection 410 is combined or blended with the projection 400. That is to say the level of pixel (i,j) is combined with the determined maximum values for each pixel (i,j), to obtain the enhanced 2D projection image 450. Said image can be reviewed by a health professional, who can analyze objects of interest 401 and underlying tissue 411 for diagnosis.

Figure 5:
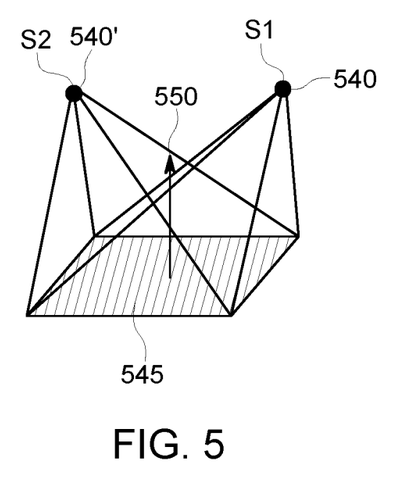
FIG. 5 shows a diagrammatic illustration of the acquisition geometry as shown in FIG. 1.

FIG. 5 shows a source detector arrangement as used for example in FIG. 1. A detector 545 is fixed in relation to the source 540. The source moves during the tomosynthesis acquisition from the source position S1 to the source position S2. Arrow 550 indicates a normal perpendicular to the detector plane and situated in the center of the plane. This normal 550 points to the source only in the zero projection. However, all other projections with α>0 are not isocentric, thus having the disadvantage that structures shift from one projection to the other.

Figure 6:
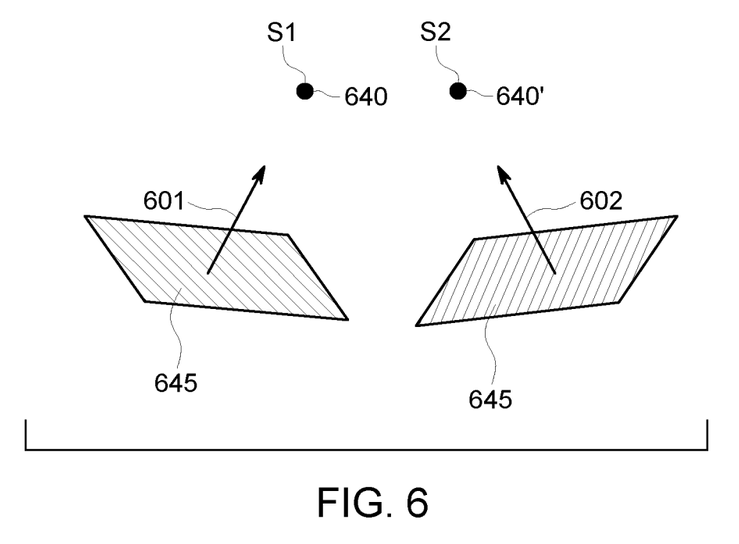
FIG. 6 shows a diagrammatic illustration of acquisition geometry according to another exemplary embodiment of the disclosure.

FIG. 6 shows a diagrammatic illustration of an acquisition geometry according to another exemplary embodiment of the disclosure. The source 640 moves as in FIG. 5 from a source position S1 to a source position S2. However, the detector's central normal points at each position S1 and S2 to the source 640 and 640', respectively. This iso-centric geometry can be provided by a virtual rotating detector. This virtual iso-centric detector allows an improved rendering of the volume, since structure shifts from one projection to the other are limited.

According to an embodiment of the disclosure each enhanced image projected on an iso-centric virtual projection are displayed successively for review. In order to reduce artifacts and noise, the tomosynthesis projection images may further be filtered and/or denoised prior to enhancing or improving the image quality.

This description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art.

What is claimed is:

1. A method for obtaining at least one enhanced image of an object of interest using a system comprising an x-ray source facing a detector, the method comprising:
    moving the x-ray source to a plurality of positions relative to the detector, the detector being stationary, and acquiring a 2D tomosynthesis projection image of the object of interest at each of the plurality of positions;
    enhancing each acquired 2D tomosynthesis projection image;
    projecting each enhanced image on an isocentric virtual detector to produce a plurality of virtual projections, wherein the normal to the isocentric virtual detector points towards the x-ray source for each position of the plurality positions to produce a plurality of virtual projections; and
    displaying successively the virtual projections.

2. The method according to claim 1, further comprising:
    enhancing a selected projection of the acquired 2D tomosynthesis projection images using at least a subset of the acquired tomosynthesis projection images at a plurality of heights, wherein a most likely height is determined for each pixel (i,j) of the selected projection image; and
    displaying the enhanced 2D projection image.

3. The method according to claim 2, wherein the enhancing step further comprises:
    for each pixel (i,j) of the selected projection image and for a given height, accumulating the values of the corresponding pixel position in at least one of the tomosynthesis projections;
    ranking the accumulated values for each pixel over all possible heights;
    determining the most likely height for each pixel (i,j) by selecting the maximum accumulated value; and
    combining (i,j)'s level with the determined maximum values for each pixel (i,j).

4. The method according to claim 3, wherein the accumulating step is performed for different frequency bands obtained by filtering the projection images.

5. The method according to claim 3, wherein the most likely height of each pixel (i,j) is obtained as a combination of maximum accumulated value and 3D marks provided by a CAD system or indicated by a user through a 3D review system.

6. The method according to claim 3, wherein the most likely height of each pixel (i,j) is stored as a height map associated to the enhanced 2D projection image.

7. The method according to claim 2, wherein the selected projection image is the central projection (0°), which is the projection perpendicular to or closest to the perpendicular of the detector.

8. The method according to claim 2, wherein at least one tomosynthesis projection image is denoised prior to improving the image quality of at least one of said at least one tomosynthesis projection image.

9. A non-transitory computer readable medium storing program instructions which, when executed by a computer, cause the computer to perform the method according to claim 2.

10. The method according claim 1, wherein the displaying step is performed at an adjustable speed.

11. A system for obtaining enhanced images of an object of interest comprising:
    an imaging system comprising an x-ray source and a detector configured to acquire 2D tomosynthesis projection images of the object of interest by moving the x-ray source to a plurality of positions relative to the detector, the detector being stationary, wherein a 2D tomosynthesis projection image is acquired at each of the plurality of positions;
    a processing unit configured enhance each of the acquired 2D tomosynthesis projection images, and project each enhanced image on an isocentric virtual detector to produce a plurality of virtual projections, wherein the normal to the isocentric virtual detector points towards the x-ray source for each position of the plurality positions to produce a plurality of virtual projections; and
    a display configured to successively display the virtual projections.

12. The system according to claim 11, wherein the object of interest is a patient's breast.

13. The system according to claim 11, wherein the system is further configured to:
    via the processing unit, compute an enhancement for a selected projection image of the acquired projection images using at least a subset of the acquired projection images at a plurality of heights, wherein a most likely height is determined for each pixel (i,j) of the selected projection image; and
    display the enhanced projection image on the display.

14. The system according to claim 13, wherein in computing the enhancement, the processing unit is further configured to:
    for each pixel (i,j) of the selected projection image and for a given height, accumulate the values of the corresponding pixel position in at least one of the tomosynthesis projections;
    rank the accumulated values for each pixel over all possible heights;
    determine the most likely height for each pixel (i,j) by selecting the maximum accumulated value; and
    combine (i,j)'s level with the determined maximum values for each pixel (i,j).

15. The system according to claim 14, wherein the most likely height of each pixel (i,j) is obtained as a combination of maximum accumulated value and 3D marks provided by a CAD system or indicated by a user through a 3D review system.

16. The system according to claim 15, wherein the most likely height of each pixel (i,j) is stored as a height map associated to the enhanced 2D projection image.

17. The system according to claim 13, wherein the selected projection image is the central projection (0°), which is the projection perpendicular to or closest to the perpendicular of the detector.

18. The system according to claim 13, wherein at least one tomosynthesis projection image is denoised prior to improving the image quality of at least one of said at least one tomosynthesis projection image.

* * * * *